(12) United States Patent
Vester

(10) Patent No.: US 10,953,213 B2
(45) Date of Patent: Mar. 23, 2021

(54) TATTOO DEVICE

(71) Applicant: Carson B. Vester, Houston, TX (US)

(72) Inventor: Carson B. Vester, Houston, TX (US)

( * ) Notice: Subject to any disclaimer, the term of this patent is extended or adjusted under 35 U.S.C. 154(b) by 0 days.

(21) Appl. No.: 16/166,934

(22) Filed: Oct. 22, 2018

(65) Prior Publication Data

US 2020/0121903 A1 Apr. 23, 2020

(51) Int. Cl.
*A61M 37/00* (2006.01)
*A01K 11/00* (2006.01)

(52) U.S. Cl.
CPC ....... *A61M 37/0076* (2013.01); *A01K 11/005* (2013.01); *A61M 2205/10* (2013.01)

(58) Field of Classification Search
CPC .......... A61M 37/0076; A61M 37/0084; A61M 37/00; A61M 2205/10; A61M 2205/103; A01K 11/005; A45D 34/04; B26F 1/28; B26F 1/24; F02P 1/083; F02P 5/05; F02P 5/06; F02P 5/07; F02P 5/075; F02P 7/06; F02P 7/063; F02P 7/0634; H01F 7/06; H01F 7/08; H01F 7/16; H01F 2007/1692
USPC .......................................................... 81/9.22
See application file for complete search history.

(56) References Cited

U.S. PATENT DOCUMENTS

| | | | |
|---|---|---|---|
| 3,317,808 A * | 5/1967 | Yott, Sr. ................... | H02P 7/066 388/837 |
| 4,671,277 A * | 6/1987 | Beuchat ............ | A61M 37/0076 606/185 |
| 4,944,776 A * | 7/1990 | Keyser ................... | B01D 53/22 95/10 |
| 5,480,381 A * | 1/1996 | Weston ................... | A61M 5/20 604/68 |
| 5,485,350 A * | 1/1996 | Hecht ....................... | H02B 1/56 165/80.3 |
| 6,033,421 A * | 3/2000 | Theiss ............... | A61M 37/0076 606/186 |

(Continued)

OTHER PUBLICATIONS

Voltage-Converter-Transformers.com, VM 1225 100V to 240V AC to 12V DC 2.5 am AC to DC converter, Nov. 21, 2015 (Year: 2015).*

(Continued)

*Primary Examiner* — Orlando E Aviles
*Assistant Examiner* — Robert F Neibaur
(74) *Attorney, Agent, or Firm* — Nolte Lackenbach Siegel

(57) ABSTRACT

A tattoo machine having a control unit and a breaker-less handheld non-magnetic tattoo device. The control unit includes a motor mount, a motor, an eccentric cam, a conductive plate, a return spring, an insulated cam follower, an electromagnetic coil controller, a motor revolutions per minute and frequency, an inverter, and a modified voltage output. The breaker-less handheld non-magnetic tattoo device is electrically connected to the modified voltage output. The breaker-less handheld non-magnetic tattoo device includes a disposable needle cartridge, a hand held actuator, an electromagnetic coil, and a power plug. The tattoo machine provides multiple deposits of ink sequentially via the disposable needle cartridge at variable speeds and variable frequencies which provide fine detailed controlled ink application at variable depths, and at variable concentrations on skin including stippling effect while simultaneously reducing hand injuries for tattoo machine operators.

15 Claims, 5 Drawing Sheets

(56) References Cited

U.S. PATENT DOCUMENTS

| | | | | |
|---|---|---|---|---|
| 7,518,479 B2* | 4/2009 | Mask | ............... | A61M 37/0084 335/212 |
| 7,908,943 B2* | 3/2011 | Beyer | ............... | A61M 37/0076 81/9.22 |
| 8,228,666 B2* | 7/2012 | Rickard | ............ | A61M 37/0076 361/679.01 |
| 8,845,550 B2* | 9/2014 | Freeman | ............ | A61B 5/15178 600/583 |
| 2003/0195542 A1* | 10/2003 | Lee | ................... | A61M 37/0076 606/186 |
| 2008/0033356 A1* | 2/2008 | Kluge | ................. | A61B 5/6885 604/117 |
| 2009/0125050 A1* | 5/2009 | Dixon | ............... | A61M 37/0076 606/186 |
| 2010/0192730 A1* | 8/2010 | Dubin | ............... | A61M 37/0076 81/9.22 |
| 2015/0352346 A1* | 12/2015 | Webb | ................ | A61M 37/0076 606/185 |
| 2016/0001054 A1* | 1/2016 | Cahill | ............... | A61M 37/0076 606/185 |
| 2018/0000419 A1* | 1/2018 | Rassman | ........... | A61M 37/0076 |
| 2020/0114137 A1* | 4/2020 | Siciliano | ........... | A61M 37/0076 |

OTHER PUBLICATIONS

Frederik Larsson, BOSCH Germany made "high rev 01011" points, ad placed Apr. 24, 2018, The Samba.com, https://www.thesamba.com/vw/classifieds/detail.php?id=2169284 (Year: 2018).*

* cited by examiner

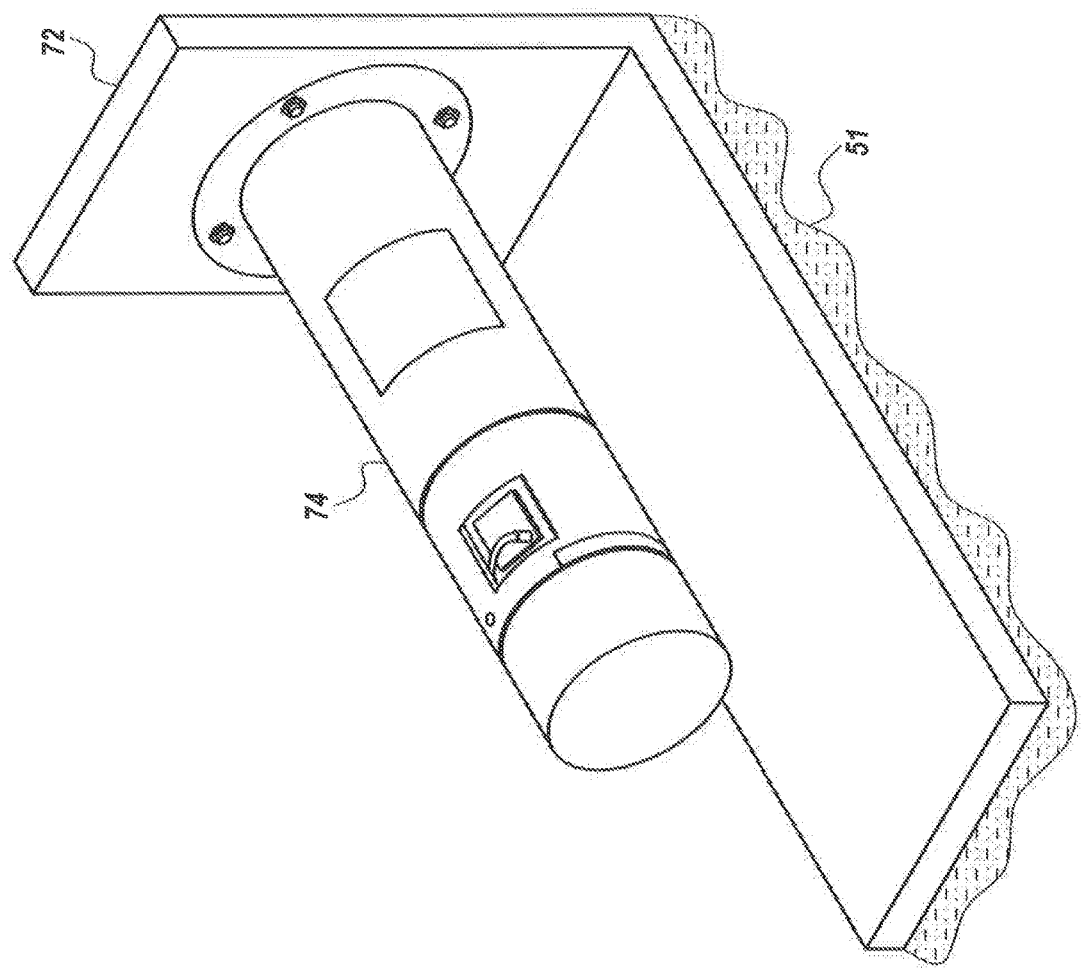

TATTOO DEVICE

FIELD

The present embodiment generally relates to a tattoo machine for inking skin, such as of humans or other animals.

BACKGROUND

A need exists for a faster safer tattoo machine
The present embodiments meet these needs.

BRIEF DESCRIPTION OF THE DRAWINGS

The detailed description will be better understood in conjunction with the accompanying drawings as follows:

FIGS. 3A and 3B depict a detailed view of the motor and eccentric cam according to one or more embodiments.

FIG. 4B depicts a section view of the breaker-less handheld non-magnetic tattoo device according to one or more embodiments.

Figure 1:
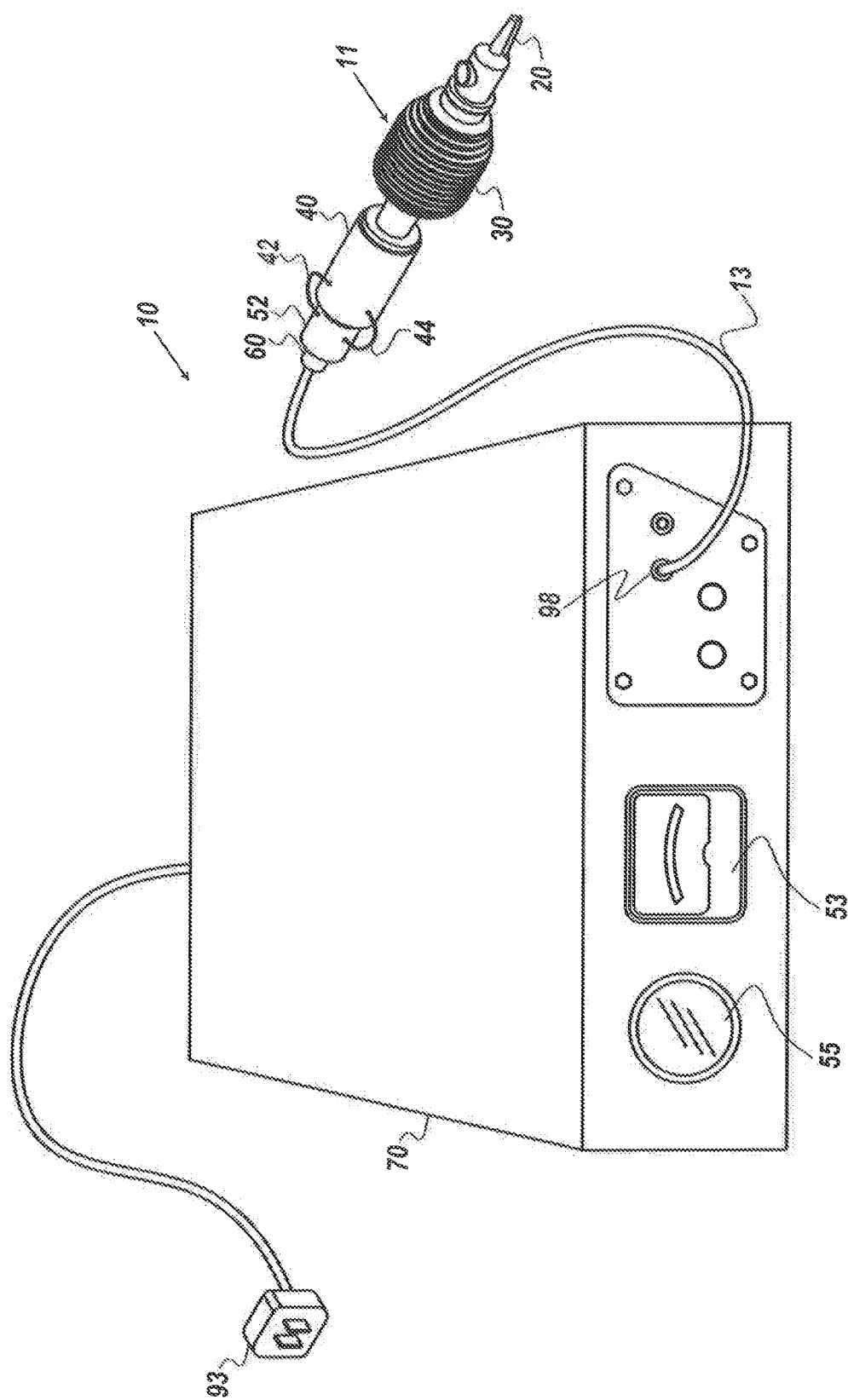
FIG. 1 depicts a diagram of the tattoo machine according to one or more embodiments.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

Specific structural and functional details disclosed herein are not to be interpreted as limiting, but merely as a basis of the claims and as a representative basis for teaching persons having ordinary skill in the art to variously employ the present invention.

The invention relates to a tattoo machine having a control unit and a breaker-less handheld non-magnetic tattoo device.

The tattoo machine detailed herein has many benefits.

The embodiments reduce the possibility of carpal tunnel syndrome for an operator by reducing the amount of time needed to perform fine stippling and fine lines while operating a tattoo machine.

Another benefit of the invention is that it reduces the possibility of shocking a customer being tattooed by the machine by having no less than three (3) separate insulated points on the device.

The invention is also beneficial because it enables reduction in waste in the tattoo process by being less messy than most tattoo machines.

Another benefit of the invention is that it uses less energy than most tattoo machines by providing control over energy usage by the operator.

The invention is also beneficial because it uses thermoplastic to reduce the need for energy required by friction internally as the electromagnetic coil actuates.

Another benefit of the invention is that it is essentially maintenance free.

A tattoo machine has a control unit.
The control unit includes a motor mount.

A motor is attached to an eccentric cam through the motor mount.

A conductive plate is mounted proximate the eccentric cam, providing a first terminal.

A return spring is mounted to the conductive plate to provide pressure through a second terminal.

An insulated cam follower is mounted to the return spring. The insulated cam follower has an insulated actuator portion for forming an e-gap in an intermittent electric circuit between the first and second terminals, when the eccentric cam is rotated by the motor.

An electromagnetic coil controller is connected to the return spring and electrically connected to a power source.

A motor revolutions per minute and frequency controller is connected to the first and second terminals simultaneously when the e-gap is closed and to the power source.

An inverter is configured to receive current from a power source and provide DC current to the electromagnetic coil controller and the motor RPM and frequency controller. The inverter is positioned electrically between the power source and the motor RPM and frequency controller and the electromagnetic coil controller.

The control unit has a modified voltage output.

The breaker-less handheld non-magnetic tattoo device is electrically connected to the modified voltage output.

The breaker-less handheld non-magnetic tattoo device includes a disposable needle cartridge with a plunger for inserting and removing a plurality of needles to deposit ink into skin.

A hand held actuator with a bore for variably actuates the disposable needle cartridge.

An electromagnetic coil with an electromagnetic bore is fastened to the hand held actuator. The electromagnetic coil has a lead wire and a ground wire. The ground wire touches the handheld actuator.

A power plug connected to the lead wire and a power cable for electrically connecting the breaker-less handheld tattoo device to the modified voltage outlet.

The tattoo machine provides multiple deposits of ink sequentially via the disposable needle cartridge at variable speeds and variable frequencies which provide fine detailed controlled ink application at variable depths, and at variable concentrations on skin including stippling effect while simultaneously reducing hand injuries for tattoo machine operators.

Turning now to the Figures, FIG. 1 depicts a diagram of the tattoo machine 10 which includes a handheld electromagnetic device for depositing ink onto skin.

The tattoo machine 10 has a control unit 70. The control unit can be ten inches in length, six inches in width, and three inches high to 15 inches in length, six inches in width and four inches high. The control unit can have a metal housing. The control unit can weigh from 8 oz. to 24 oz.

A breaker-less handheld tattoo device 11 is electrically connected to a modified voltage output 98 of the control unit 70. The electrical connection can be a flexible two wire insulated or non-insulated copper wire 13. The voltage range through the wire 13 can be from three volts to 15 volts DC.

The copper wire 13 can be an 18 gauge unbranded cooper wire made in China.

The breaker-less handheld tattoo device 11 has a disposable needle cartridge 20 for inserting and removing a plurality of needles to insert ink into skin; The needle cartridge can be a CHEYENNE cartridge from Germany.

In embodiments, the disposable needle cartridge can have from one to 26 needles and an ink inlet port that provides gravity fed ink to the needles.

In embodiments, six to 14 needles can be used, and all the numbers in between.

The breaker-less handheld tattoo device 11 has a hand held actuator 30 for variably actuating the disposable needle cartridge 20. The hand held actuator can be from four to eight inches long which is from the tip of the needle cartridge 20 to the power plug 60. The hand held actuator can have an outer diameter from one to 2.5 inches. The hand held actuator can be made from alloys, stainless steels, or thermoplastics. The hand held actuator can weight from 5 oz. to 16 oz.

The breaker-less handheld tattoo device 11 has an electromagnetic coil 40 fastened to the hand held actuator. The electromagnetic coil can be from 26 AUG to 22 AUG electromagnet wire. The electromagnetic coil wire can be made of copper or silver. The electromagnetic coil 40 can vary in length from six wraps to 12 wraps depending on wire gauge.

The electromagnetic coil can have a voltage range from three volts DC to 15 volts DC draw amperage from 0.5 AMP to 1.5 AMP.

The electromagnetic coil 40 has a lead wire 42 and a ground wire 44, wherein the ground wire touches the handheld actuator 30.

The lead wire 42 connecting the electromagnetic coil 40 to a terminal adapter 52 for connects the power plug to the electromagnetic coil 40. The lead wire 42 can be from 0.25 to 1 inch in length and can be a copper wire with a plastic, scratch resistant insulation. The lead wire can sustain surges from 0.5 to 3 AMP.

The terminal adapter 52 can be made from brass, aluminum, stainless steel, or thermoplastics.

The terminal adapter can receive assorted electrical connections. The terminal adapter can receive an RCA™ type connection or NEUTRIK NYS228 Stereo ¼" PLUGS™ type connection.

A power plug 60 engages the terminal adapter 52 and a lead wire 42 for conveying power from the modified voltage output 98 of the control unit.

The power plug 60 can have a voltage range from 3-15 volts DC.

A window 55 for viewing motor performance interior of the control unit 70 is labelled to view equipment while operating the tattoo machine.

The window 55 can be circular, rectangular, or trapezoidal.

The size of the window 55 can be from one inch to three inches in diameter. The window can be from one to three inches long and from one inch to three inches tall.

The window 55 can be from 0.125 to 0.250 inch thick.

The window 55 can be made of polycarbonate, and can be clear or colored as long as it is transparent.

A current gauge 53 presenting current through the control unit is also labelled. The current gauge can be 0.75 to 2 inches in diameter. The current gauge can be made of plastic and metal, can weigh from 2 to 6 oz., and can handle a current from 0.001 to 5 AMP.

A power source 93 is also shown.

Figure 2:
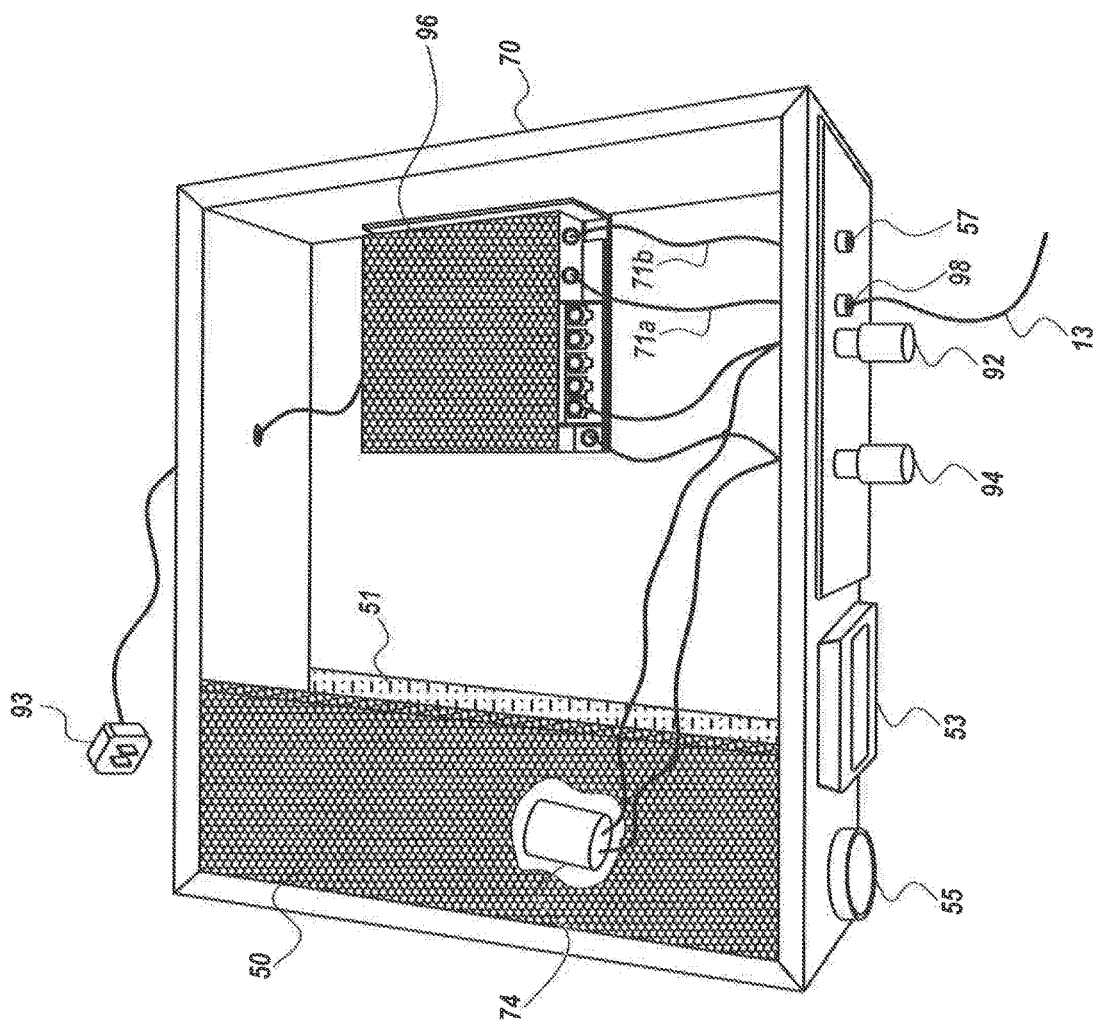
FIG. 2 depicts a diagram of a portion of the control unit according to one or more embodiments.

FIG. 2 depicts a diagram of a portion of the control unit 70.

Inside the control unit 70 is a motor 74 and an inverter 96.

The inverter 96 is configured to receive A/C current from a power source 93 and provide DC current 71a to the electromagnetic coil via a power cable 13 via a modified voltage output 98 and DC current 71b to a direct variable voltage outlet 57.

The inverter 96 can be from 1×3×3 to 3×6×9 inches. The inverter 96 can be made of plastic or metal with aluminum heat sinks and perforated material to allow air to cool the unit. The inverter 96 can have AC connections to a wall from 110 to 220 volts AC, and can step down voltages from three volts DC to 24 volts DC.

The modified voltage output 98 can be from three volts DC to 24 volts DC.

The control unit 70 provides a motor revolutions per minute (RPM) and frequency controller 94. The inverter 96 is positioned electrically between the power source 93 and the motor RPM and frequency controller 94 and the electromagnetic coil controller 92.

The motor RPM and frequency controller 94 can be an NPN 3-35 volts PWM Regulator™, Made in China.

The control unit 70 provides a direct variable voltage outlet 57.

The control unit 70 provides an electromagnetic coil power controller 92 connected to the inverter 96.

The power controller 92 can be a NPN 3-35 volt Regulator™, Made in China.

A window 55 is shown for viewing the motor performance interior of the control unit while operating the tattoo machine.

A current gauge 53 presenting current through the control unit 70 is shown.

A perforated lid 50 with motor vibration insulation 51 is also shown.

The perforated lid 50 can be from 4×8 to 6×12 inches and 0.125 inch thick with 0.125 inch perforated holes.

The perforated lid 50 can be made from aluminum or stainless steel.

The motor vibration insulation 51 can be fire resistant carpet padding.

Figure 3B:
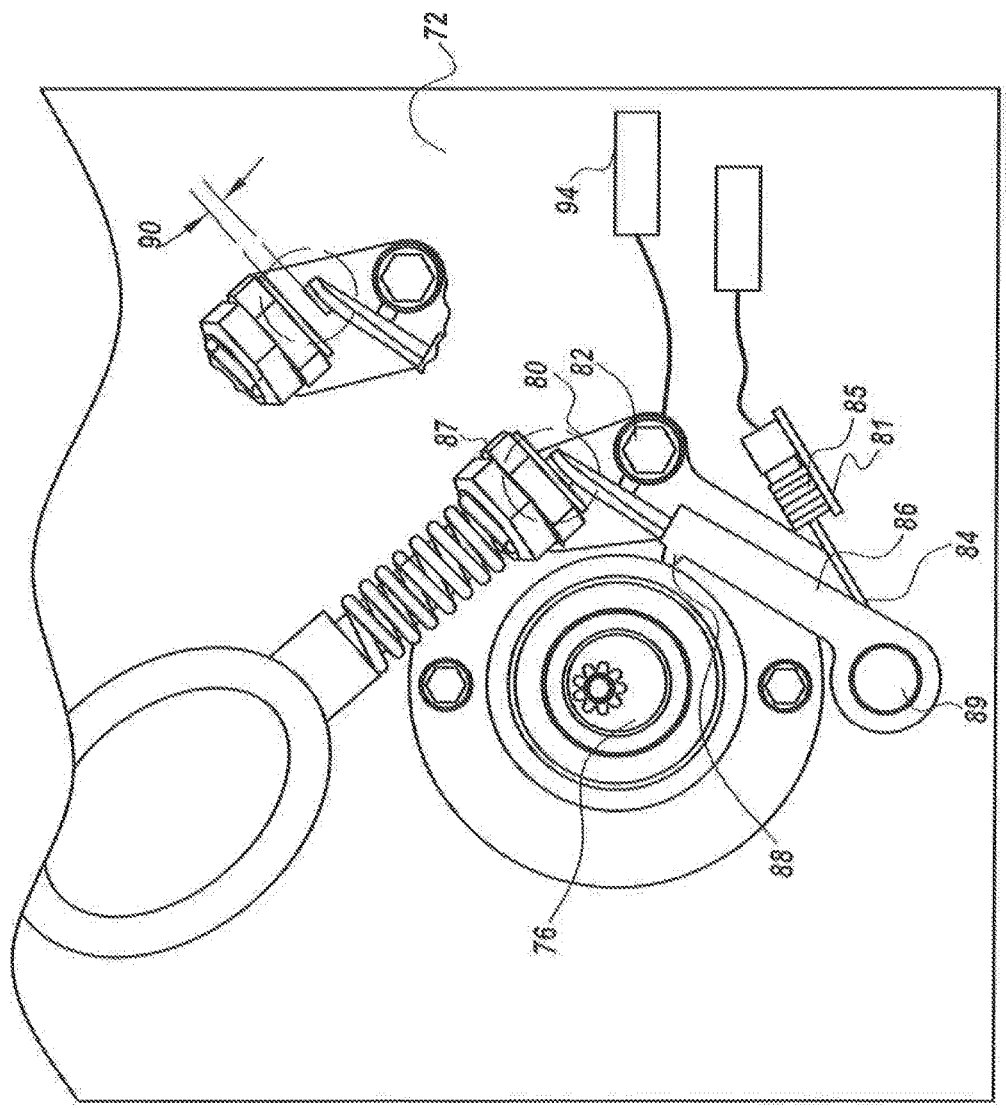

FIGS. 3A and 3B depict details of the motor and eccentric cam according to embodiments.

A motor mount 72 is shown.

The motor mount 72 can be from 0.125 to 0.5 inch thick, 1 to 3 inches wide, and from 4 to 8 inches long. The motor mount 72 can be bent at an angle from 10 to 90 degrees.

The motor mount 72 can be made from poly carbonate, aluminum, or steel.

The motor mount 72 can weigh from 1 to 12 oz.

A motor 74 is attached to an eccentric cam 76 through the motor mount 72.

The motor 74 can be a permanent magnet motor, 3 to 24 volts DC, and can have a RPM range from 200-10,000 RPM.

The eccentric cam 76 can be connected to the motor 74 on one side of the motor mount 72 and the motor 74 can be positioned on an opposite side of the motor mount 72.

The eccentric cam 76 can be made from peek. The eccentric cam can be offset from 0.010 to 0.040 inches from center line. A roller bearing can complete the eccentric cam assembly reducing friction at the insulated actuator portion 88.

In embodiments, the motor mount 72 is an L shaped plate and of a non-magnetic, non-metal material.

In embodiments, the motor 74 provides from 500 to 5000 revolutions per minute.

A conductive plate 80 can be mounted proximate the eccentric cam 76 providing a first terminal 82.

The control unit 70 includes a return spring 84 mounted to the conductive plate 80 providing pressure through a second terminal 85.

An insulated cam follower 86 mounted to the return spring 84 in the control unit has an insulated actuator portion 88 for forming an e-gap 90 in an electric circuit formed between the first and second terminals when the eccentric cam 76 is rotated by the motor 74.

In embodiments, the return spring 84 conductive plate 80, second terminal 85, cam follower 86, actuator portion 88, first plate extension 81, post 89, and e-gap 90 can all be a part of a breaker point assembly. The breaker point assembly can be a BOSH 01011™ made in Germany.

The electromagnetic coil controller can be connected to the return spring 84 and electrically connected to a power source.

It should be noted that the motor revolutions per minute and frequency controller 94 is connected to the first terminal 62 and second terminal 85 simultaneously when the e-gap 90 is closed and to the power source.

The tattoo machine provides multiple deposits of ink sequentially via the disposable needle cartridge at variable speeds and variable frequencies, which provide fine detailed controlled ink application at variable depths, and at variable concentrations on skin including stippling effect while simultaneously reducing hand injuries for tattoo machine operators.

In embodiments, the eccentric cam is mounted from 0.01 to 0.1 millimeters off center of the cam.

In embodiments, the conductive plate 80 has a first plate extension 81 supporting the first terminal 82, and a second plate extension 87 supporting the second terminal 85, and a post 89 configured to provide support as the return spring 84 pivots around the post 89.

In embodiments, the return spring 84 is a V shaped metal component.

In embodiments, the insulated cam follower 86 comprises a member of the group: a plastic, a rubber, a thermoplastic or combinations thereof.

Figure 4A:
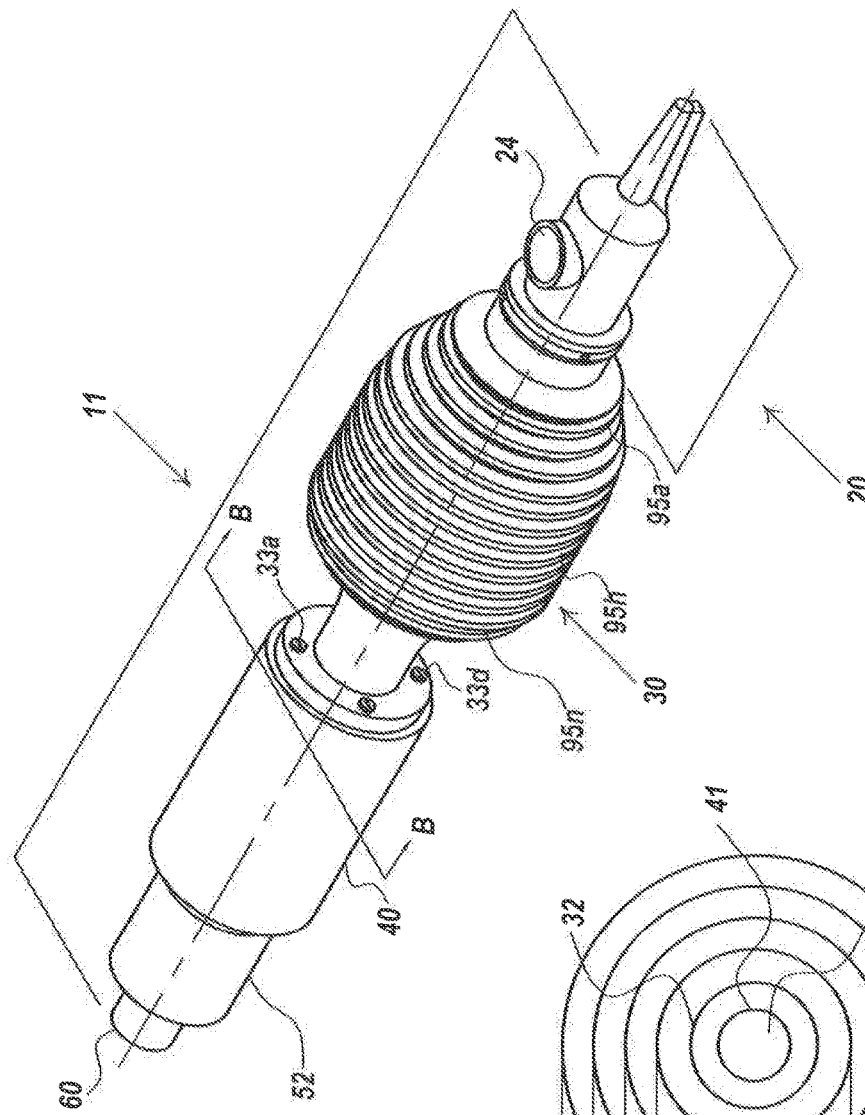
FIGS. 4A and 4B depicts a detailed view of the breaker-less handheld non magnetic tattoo device according to one or more embodiments.
Figure 4B:
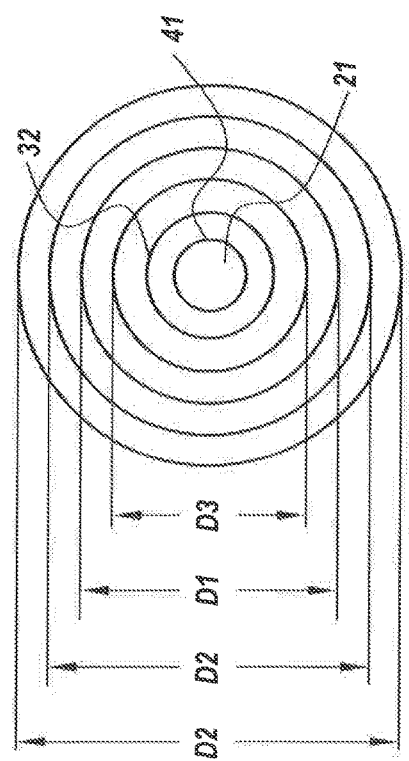

FIGS. 4A and 4B depicts a detail of the breaker-less handheld tattoo device 11 and a section view along cut lines A-A.

The breaker-less handheld tattoo device 11 is electrically connected to a modified voltage output of the control unit via a wire.

The voltage output can be from 3 volts DC to 24 volts DC.

The breaker-less handheld tattoo device 11 has a disposable needle cartridge 20 with a plunger 21, for inserting and removing a plurality of needles to insert ink into skin.

The needle cartridge 20 can be a CHEYENNE Model #: CHC-3RL™ or Patent Made in Germany.

The plunger 21 can be made of a thermoplastic PEEK or xp100 PEEK. The plunger can have a diameter from 0.25 to 0.375 inches, and can have a length from 2 to 4 inches.

The plunger 21 can make a mechanical connection between the coil device and the needle cartridge assembly.

The breaker-less handheld tattoo device 11 has a hand held actuator 30 with a bore 32 shown in the cross section, for variably actuating the disposable needle cartridge 20.

The hand held actuator has from 3 to 20 helical fins 95a-95n disposed around the body for providing a ground.

In embodiments, the bore 32, can be made from aluminum, brass or stainless steel. The bore can carry a tolerance from 0.003 to 0.007 inches, and can be from 2 to 4 inches.

In embodiments, the bore 32 can carry the plunger 21 which can make a mechanical connection between the electromagnetic coil 40 and the needle cartridge 20.

The breaker-less handheld tattoo device 11 has an electromagnetic coil 40 with an electromagnetic bore 41 (shown in the cross section) fastened to the hand held actuator.

The electromagnetic bore 41 can be made from a non-Ferris material such as plastic, and can be from 0.25 to 0.375 inches in diameter and from 1 to 2 inches long.

In embodiments, the electromagnetic bore 41 can induce a current to attract the plunger 21 from 0.375 to 1.5 AMP.

The electromagnetic coil 40 has a lead wire and a ground wire, wherein the ground wire touches the handheld actuator 30.

The ground wire can be an 18 gauge copper wire that can be insulated and can be from 0.5 to 2 inches long.

In embodiments, the ground wire can be from 3 to 24 volts DC and can carry an amperage from 0.375 to 1.5 AMP.

In embodiments, the disposable needle cartridge has from 3 to 20 needles and an ink inlet port 24 that provides gravity fed ink to the needles.

In embodiments, the hand held actuator 30 has from 3 to 20 helical fins disposed around the body for providing a ground.

In embodiments, the tattoo machine has a plunger actuator 101 disposed inside the bore 32 of the hand held actuator 30 for moving a plunger of the disposable needle cartridge.

In embodiments, the plunger actuator 101 can be made of a Ferris material to carry an electromagnetic flux to do linear work.

In embodiments, the electromagnetic coil and be a solenoid with solenoid plunger or a relay with relay plunger, wherein the solenoid with solenoid plunger or relay with relay plunger engages the plunger of the disposable needle cartridge.

The electromagnetic coil 40 can be attached to fasteners 33a-33d.

In embodiments, the fasteners can be a 4-40 screw or a hex head or cap screw.

The power plug 60 and terminal adapter 52 are shown, wherein the terminal adapter 52 for connects the power cable to the electromagnetic coil 40.

Example 1

The control unit 70 is plugged into an AC current, such as a wall plug.

A breaker-less handheld non-magnetic tattoo device is electrically connected to a modified voltage outlet 98 of the control unit 70.

A disposable needle cartridge 20 with a plunger 21 is attached to a hand held actuator 30 with a bore 32 of a breaker-less handheld non-magnetic tattoo device 10 creating an electrical connection to the modified voltage outlet 98.

The motor RPM and frequency controller 94 of the control unit 70 is turned on.

An operating voltage is applied to an electromagnetic coil controller 92.

The plurality of needles of the disposable needle cartridge begin reciprocating action.

The disposable needle cartridge is dipped into an ink supply and the Tattoo process into the skin is initiated providing deposits of ink sequentially via the disposable needle cartridge at variable speeds and variable frequencies which provide fine detailed controlled ink application at variable depths, and at variable concentrations on skin including stippling effect while simultaneously reducing hand injuries for tattoo machine operators.

Example 2

An exemplary tattoo machine has a motor mount that is hard plastic and L shaped which is 3 inches tall and 5 inches long.

A variable speed DC motor is used which runs on 3 and 15 volts is a is attached to an eccentric cam is 0.5 inches long 0.040 of an inch offset from center through the motor mount.

A breaker point assembly is used with a conductive plate can be L shaped and 1 inch by ½5 inches dimensions. The conductive plate creates a first terminal using a screw.

A V shaped return spring that is 0.018 thick with a Rockwell hardness of 52 provides resistance form an initial opening of 60 degrees to a reduced opening of 40 degrees is mounted to the conductive plate provides pressure through a second terminal that is also a screw. Each screw can have a shaft of 0.25 inches and 440 thread pitch.

An insulated cam follower made from hard thermoplastic of PEEK (polyethylene ethyl ketone) XP 100 mounted to the return spring.

The wear resistant PEEK is shaped into an insulated cam follower having an insulated actuator portion that is the form of a triangle for forming an e-gap that is a gap breaking the electric circuit forming an intermittent electric circuit between the first and second terminals. The e-gap can be a width of 0.040 inch, when the eccentric cam 76 is rotated by the motor 74 and the insulated actuator portion opens the e-gap.

An solenoid type electromagnetic coil controller is connected to the return spring and electrically connected to the inverter through electromagnetic coil controller 92 and one of the wires from the power source 93.

A motor revolutions per minute and frequency controller can be from 3 volts to 3.5 volt commercial controller from MPN, China is connected to the first and second terminals simultaneously when the e-gap is closed and to the power source.

An Ace electronics AC/DC inverter for 110 AC current is configured to receive current from a power source and provide 3 volts DC to 20 volts DC current to the electromagnetic coil controller and the motor RPM and frequency controller with the inverter positioned electrically between the power source and the motor RPM and frequency controller and the electromagnetic coil controller.

Installed in the control unit is a modified voltage output 98, which connects to the inverter and power cable 13.

A hand held a breaker-less handheld tattoo device is electrically connected to the modified voltage output by the power cable 13.

The breaker-less handheld tattoo device uses a 7 disposable needle cartridge with a plunger 21 for inserting and removing a plurality of needles to deposit organic, soy based ink into skin.

A hand held actuator which is 1.37 inches at the widest outer diameter has with an inner bore of 0.312 inches or variably actuating the disposable needle cartridge.

A solenoid type electromagnetic coil with an outer diameter of 1.25 inches has an electromagnetic bore with a 0.312 inner diameter is fastened to the hand held actuator.

A lead wire and a ground wire from the electromagnetic coil touch the handheld actuator.

A conventional, commercial power plug connects to the lead wire, and a power cable for electrically connecting the breaker-less handheld tattoo device to the modified voltage outlet; and wherein the tattoo machine provides multiple deposits of ink sequentially via the disposable needle cartridge at variable speeds and variable frequencies using the intermittent electric circuit which provides fine detailed controlled ink application at variable skin depths, and at variable ink concentrations on skin while simultaneously reducing hand injuries for tattoo machine operators.

While these embodiments have been described with emphasis on the embodiments, it should be understood that within the scope of the appended claims, the embodiments might be practiced other than as specifically described herein.

What is claimed is:

1. A tattoo machine, comprising:
    a control unit comprising:
        a motor mount;
        a motor attached to an eccentric cam through the motor mount;
        a conductive plate mounted proximate the eccentric cam providing a first terminal;
        a return spring mounted to the conductive plate to provide pressure and provide intermittent conductivity through a second terminal, an insulated cam follower mounted to the return spring, the insulated cam follower having an insulated actuator portion for forming an e-gap in an intermittent electric circuit between the first terminal and the second terminal when the eccentric cam is rotated by the motor;
        an electromagnetic coil controller connected to the return spring and electrically connected to a direct current power source;
        a motor revolutions per minute and frequency controller connected to the first terminal and the second terminal simultaneously when the e-gap is closed and to the direct current power source;
        an inverter configured to receive alternating current (AC) from an AC power source and provide direct current (DC) to the electromagnetic coil controller and the motor revolutions per minute (RPM) and frequency controller, the inverter positioned electrically between the AC power source and the motor RPM and frequency controller and the electromagnetic coil controller; and
        a modified voltage output to provide 3 volts to 24 volts DC output;
    a breaker-less hand-held tattoo device connected to and controlled by the control unit using the DC from the modified voltage output of the control unit, the breaker-less hand-held tattoo device comprising:
        a disposable needle cartridge with a plunger for inserting and removing a plurality of needles to deposit ink into skin;
        a hand-held actuator with a bore fastened to the plunger for variably actuating the disposable needle cartridge;
        an electromagnetic coil with an electromagnetic bore fastened to the hand-held actuator, the electromagnetic coil having a lead wire and a ground wire, the ground wire touching the hand-held actuator, wherein the electromagnetic coil is configured to initiate movement of the plunger;
        a power plug connected to the lead wire, and a power cable for electrically connecting the breaker-less hand-held tattoo device to the modified voltage output of the control unit; and
    wherein the tattoo machine is configured to provide multiple deposits of ink sequentially via the disposable needle cartridge at variable speeds and variable frequencies using the intermittent electric circuit which provides fine detailed controlled ink application at variable skin depths, and at variable ink concentrations on skin while simultaneously reducing hand injuries for tattoo machine operators.

2. The tattoo machine of claim 1, wherein the control unit comprises at least one of:
   a perforated lid;
   a motor vibration insulation;
   a current gauge;
   a window for viewing motor performance while operating the tattoo machine; and
   a direct variable voltage outlet.

3. The tattoo machine of claim 1, wherein the motor mount is an L-shaped plate and of a non-magnetic, non-metal material.

4. The tattoo machine of claim 1, wherein the motor provides from 500 to 5000 revolutions per minute.

5. The tattoo machine of claim 1, wherein the eccentric cam is mounted from 0.01 to 0.1 millimeters off of the center of the cam.

6. The tattoo machine of claim 1, wherein the conductive plate has a first plate extension supporting the first terminal, and a second plate extension supporting the second terminal, and a post configured to provide support as the return spring pivots around the post.

7. The tattoo machine of claim 1, wherein the return spring is a V shaped metal component.

8. The tattoo machine of claim 1, wherein the insulated cam follower is made of a material that comprises a member of the group: plastic, rubber, thermoplastic or combinations thereof.

9. The tattoo machine of claim 1, wherein the electromagnetic coil controller has a frequency from 60 to 150 hertz.

10. The tattoo machine of claim 1, wherein the motor revolutions per minute and frequency controller has a range from 200 to 10,000 rpm.

11. The tattoo machine of claim 1, wherein the inventor is a 100-200 volt A/C to 6-24 volt DC inverter.

12. The tattoo machine of claim 1, wherein the disposable needle cartridge has from 1 to 26 needles and an ink inlet port that provides gravity fed ink to the needles.

13. The tattoo machine of claim 1, wherein the hand-held actuator has from 3 to 20 helical fins disposed around the body for providing a ground.

14. The tattoo machine of claim 1, comprising a terminal adapter for connecting the power cable to the electromagnetic coil.

15. The tattoo machine of claim 1, wherein the electromagnetic coil is a solenoid with solenoid plunger or a relay with a relay plunger, wherein the solenoid plunger or the relay plunger is configured to engage the plunger of the disposable needle cartridge.

* * * * *